US012599394B2

(12) United States Patent
Braun

(10) Patent No.: US 12,599,394 B2
(45) Date of Patent: Apr. 14, 2026

(54) SURGICAL INSTRUMENT WITH A HANDLE

(71) Applicant: Tuebingen Scientific Medical GmbH, Tübingen (DE)

(72) Inventor: Marcus Braun, Weil im Schönbuch (DE)

(73) Assignee: Tuebingen Scientific Medical GmbH (DE)

( * ) Notice: Subject to any disclaimer, the term of this patent is extended or adjusted under 35 U.S.C. 154(b) by 309 days.

(21) Appl. No.: 18/199,104

(22) Filed: May 18, 2023

(65) Prior Publication Data

US 2023/0371970 A1 Nov. 23, 2023

(30) Foreign Application Priority Data

May 19, 2022 (DE) .......................... 102022112562.9

(51) Int. Cl.
*A61B 17/29* (2006.01)
*A61B 17/3201* (2006.01)

(52) U.S. Cl.
CPC ...... *A61B 17/2909* (2013.01); *A61B 17/3201* (2013.01); *A61B 2017/2903* (2013.01);
(Continued)

(58) Field of Classification Search
CPC ............ A61B 17/29–295; A61B 17/30; A61B 17/320016–320036; A61B 17/32056;
(Continued)

(56) References Cited

U.S. PATENT DOCUMENTS 5,700,275 A 12/1997 Bell et al.
9,655,636 B2 5/2017 Stefan et al.
(Continued)

FOREIGN PATENT DOCUMENTS

DE 19647761 C1 1/1998
EP 2377477 A1 5/2012
EP 2532315 A1 12/2012

OTHER PUBLICATIONS

German Search Report for German Application No. 10 2022 112 562.9, with partial English translation, dated Dec. 21, 2022, 11 pages.
(Continued)

*Primary Examiner* — Elizabeth Houston
*Assistant Examiner* — Jonathan A Hollm
(74) *Attorney, Agent, or Firm* — Buchanan Ingersoll & Rooney PC

(57) ABSTRACT

A surgical instrument with a handle, a shaft extending from the handle into a distal direction, and an effector, preferably a (medical/surgical) forceps or a scissor, at a distal end of the shaft. The handle comprises a plurality of manual actuating members being adapted to manipulate the effector for rotating, tilting and open-closing movements. The plurality of manual actuating members comprise a first actuating member being rotatable around a rotational axis, which is a longitudinal axis of the shaft or that is parallel offset to the longitudinal axis, and a second actuating member being rotatable around a rotational axis, which is identical to the rotational axis of the first actuating member or is parallel offset thereto and being movable (axially) along the longitudinal axis of the shaft.

15 Claims, 5 Drawing Sheets

(52) U.S. Cl.
CPC ................. *A61B 2017/2927* (2013.01); *A61B 2017/2946* (2013.01)

(58) Field of Classification Search
CPC ................. A61B 17/26; A61B 17/221; A61B 17/22031–22032; A61B 2017/320024–320064; A61B 2017/2212–2217; A61B 2017/22034–22035; A61B 18/1442–1447; A61B 2018/145–1462
See application file for complete search history.

(56) References Cited

U.S. PATENT DOCUMENTS

| | | | |
|---|---|---|---|
| 2002/0177874 A1* | 11/2002 | Nicholas | ............ A61B 17/0218 606/206 |
| 2009/0306658 A1* | 12/2009 | Nobis | ................ A61B 18/1482 606/46 |
| 2013/0041403 A1 | 2/2013 | Cunningham et al. | |
| 2019/0307475 A1 | 10/2019 | Kitamura et al. | |
| 2021/0008341 A1 | 1/2021 | Landey et al. | |
| 2021/0370023 A1 | 12/2021 | Khuu et al. | |

OTHER PUBLICATIONS

Extended European Search Report for European Application No. 23173975.6, dated Sep. 12, 2023, 7 pages.

* cited by examiner

SURGICAL INSTRUMENT WITH A HANDLE

This application claims priority to and the benefit of German Patent Application No. DE 10 2022 112 562.9 filed May 19, 2022, which is incorporated by reference herein.

TECHNICAL BACKGROUND

The present disclosure relates to a surgical instrument especially for minimally invasive surgery.

Medical or surgical instruments such as forceps or scissors are used for minimally invasive surgery. Minimally invasive surgery is less traumatic than open surgery for a patient and requires shorter recovery times and thus causes significantly lower treatment costs.

Surgical instruments for minimally invasive surgery are well known from the prior art. A surgical instrument according to prior art is disclosed in EP 2 377 477 B1 for example and is shown in FIG. 1. The surgical instrument comprises a proximal handle, a shaft extending in a distal direction from the handle, and an effector at the distal end section of the shaft. The effector can be a (medical) forceps or scissor. The handle comprises an ergonomically shaped handle piece, which is mounted in an inclinable manner to a coupling member via a hinge mechanism. The coupling member is pivotably connected to the shaft. The handle piece comprises a first manipulator in the form of a rotary knob and a second manipulator in the form of a handle lever or trigger. Thus, the surgical instrument comprises operating mechanisms for three independent movements of the effector. Actuation of the handle lever or trigger actuates the effector, preferably opens or closes the jaws of the effector. A pivoting or inclining movement of the handle piece deflects the distal end section of the shaft including the effector. A rotational movement of the rotary knob rotates the distal end section around its longitudinal axis. Furthermore, the shaft can be rotated relative to the proximal handle by rotating a second rotary knob.

The distal end section including the effector follows the movement of the wrist during deflection. However, to achieve the full functionality of the surgical instrument, the user needs to actuate multiple operating mechanism at once. For example, the user must incline or pivot the handle piece to deflect the distal end section and at the same time rotate the rotary knob to rotate the distal end section. Therefore, precise control of the individual manipulators is difficult and forces the user to hold his hand in an uncomfortable position. More concrete, holding the surgical instrument forces the user in a constrained posture. When the user releases the handle piece, the distal end section returns to its original position. Furthermore, the second rotary knob rotating the shaft can be difficult to reach with only one hand.

Therefore, it is preferable to operate every operating mechanism sequentially or independently from each other. There is further a need to hold the effector in its position, when the effector is either deflected or closed.

DE 19 647 761 C1 discloses an endoscope with a handle and a distal effector. The handle comprises three actuating elements. Two of the actuating elements are rotary knob that are arranged behind each other and are rotatable around the same rotational axis. A rotation of the first rotary knob rotates the distal end section around the longitudinal axis of the shaft. A rotation of the second rotary knob bends the distal end section in a bending plane. The handle further comprises a lever that is actuated by the palm of the user. Actuation of the lever actuates the distal effector, i.e. opens or closes the jaws of the forceps.

However, for a good user experience/good operability of the instrument, it is advantageous to provide an instrument with only two actuating elements.

SUMMARY OF THE DISCLOSURE

In view of the disadvantages of the state of the art, it is the objective of the present disclosure to overcome the disadvantages of the state of the art, in particular to provide a surgical instrument with improved operability enabling a user to operate the surgical instrument with one hand.

The present disclosure relates to a surgical instrument with a (proximal) handle, a shaft extending from the handle into a distal direction, and an effector, preferably a (medical/surgical) forceps or a scissor, at a distal end section of the shaft. The handle comprises a plurality of manual actuating members being adapted to manipulate the effector for rotating, tilting and open-closing movements. The plurality of manual actuating members consists of a first actuating member and a second actuating member. The first actuating member is rotatable around a rotational axis, which is a longitudinal axis of the shaft or that is parallel offset to the longitudinal axis. The second actuating member being rotatable around a rotational axis, which is identical to the rotational axis of the first actuating member or is parallel offset thereto and being movable (axially) along the longitudinal axis of the shaft.

The actuating members of the surgical instrument cause different movements of the distal end section of the shaft including the effector. Every movement of the actuating members causes a different and independent movement of the distal end section or the distal effector. The different movements of the distal tip are a rotation around the longitudinal axis of the shaft and a tilting or bending movement in a tilting or bending plane. Further, the effector, preferably the forceps or scissor, can be opened and closed. For the movements of the distal end section, the two actuating members are provided at the handle. The two actuating members are arranged next to each other, preferably in a longitudinal axis that is identical to the longitudinal axis of the shaft and of the handle. The first actuating member is rotatable around the axis; the second actuating member is also rotatable around the axis. Therefore, the two actuating members are preferably rotatable around the same rotational axis. Additionally, the second actuating member is moveable axially or translationally along the longitudinal axis. The axial movement of the second actuating member is independent of the rotational movement of the second actuating member. The second actuating member can be moved from a distal position to a proximal position and back.

To summarize, the core of the present disclosure is to steer every movement of the distal end section of the shaft and the effector at the distal with only the two actuating members that are operable with only one hand.

The surgical instrument has the following advantages. The user can hold and operate the surgical instrument with only one hand. The handles are arranged in a way that the user must not change his grip during operation of the surgical instrument. The user can reach all actuating members and execute all possible movements of the actuating members without changing the position of the grip. Furthermore, only two the two actuating members are necessary to operate the surgical instrument. The two actuating members can be actuated independently from each other. The different movements of the effector can be activated sequentially. Especially, the user must not hold one of the actuating members while actuating or moving the other one. This simplifies operating the surgical instrument.

Advantageous aspects of the present disclosure are part of the attached sub claims.

Preferably, the (axial) movement of the second actuating member along the longitudinal axis of the shaft actuates the distal effector, preferably opens or closes the jaws of the forceps. Sliding of the second actuating member in an axial direction causes the opening/closing movement of the effector. It is very easy to actuate the effector. The user does not need to change its grip on the handle to open or close the effector.

Preferably, the effector is open when the second actuating member is in its distal position and the effector is closed when the second actuating member is in its proximal position. Therefore, the effector can be closed by pulling the second actuating member towards the user. That provides intuitive handling of the effector for the user/operator.

Preferably, the second actuating member is connected to a locking spring in an axially fixed manner. The second actuating member can move the locking spring at least during a movement from the distal to the proximal position. The second actuating member may comprise an actuating wheel and a collar extending from the actuating wheel in a proximal direction. The collar may comprise a shoulder that engages with the locking spring and moves the locking spring axially. Preferably, the locking spring is axially moveable independently from the collar, when the second actuating member is in the proximal position.

The locking spring may comprise a round main body that is positioned concentrically to the longitudinal axis of the handle. Two locking arms extend in the distal direction from the main body. The locking arms are arranged on diametrically opposite sides of the longitudinal axis.

Preferably, the locking spring is connected to a (wire) spring in an axially fixed manner and the axial movement of the locking spring compresses the spring. The locking spring may be connected to the spring such that the axis of the axial movement of the locking spring corresponds to a longitudinal axis of the spring. When the spring is fully compressed, it is moved in the axial direction, too. When the distal end section of the shaft is tilted, the distance between the distal end section with the effector and the second actuating member changes. The spring can vary its longitudinal extension and is able to compensate the change in distance.

The spring provides a resistance for the user when pushing the second actuating member to the proximal position. Additionally, the spring pushes the second actuating member back to its distal position when the effector is opened by the user.

Preferably, the spring is connected to a connector or a connecting member in an axially fixed manner. The connector can move axially with the axial movement of the spring. The connector may comprises a base plate on which the spring is attached. When the locking spring is moved axially and the spring is compressed, the connector is also moved in the axial direction.

Preferably, the connector comprises an elongated base member that is connected to an actuation tube in an axially fixed manner. The elongated base member is a tube that surrounds the actuation tube. That means that the actuation tube is moved axially, when the connector is moved. Preferably, the actuation tube extends along the shaft of the surgical instrument and is connected to the effector at its distal end section. Therefore, an (axial) movement of the actuation tube actuates the distal effector.

To sum up, the axial movement of the second actuating member may be transmitted to the actuation tube via the locking spring, the (compressed) wire spring and the connector. The axial movement of the actuation tube actuates the effector, preferably closes the jaw parts of the effector with a movement in the proximal direction and preferably opens the jaw parts with a movement in the distal direction.

According to an advantageous aspect of the present disclosure, a rotation of the first actuating member around its rotational axis tilts/bends the distal end in a tilting or bending plane. That means the distal end section of the shaft does not extend in the direction of the longitudinal axis of the shaft but rather comprises a tilting angle between the extension (or longitudinal axis) of the distal end section and the longitudinal axis of the rest of the shaft. The tilting movement allows the effector to reach places inside the patient's body cavities that would not be accessible with a straight shaft. The first actuating member is self-locking that the distal end section does not return in its initial position from the tilted position, when the user releases the first actuating member. Therefore, the user can release the first actuating member and actuate the second actuating member sequentially.

Preferably, the first actuating member is connected to a spindle/leadscrew in a rotatable manner transmitting the rotation of the first actuating member into a translational/axial movement. The first actuating member is mounted inside the housing of the handle in a rotatable manner.

Preferably, the leadscrew is connected to a tilting tube extending in the shaft that moves axially along the longitudinal axis of the shaft. The leadscrew transmits the rotation of the first actuating member into the translational/axial movement of the tilting tube. The tilting tube may extend along the shaft inside a hollow shaft tube.

Preferably, the axial movement of the tilting tube actuates tilts the distal end section. The tilting tube may protrude from the shaft. When the tilting tube is pushed in the distal direction by the axial movement of the leadscrew, the tilting tube pushes a lever in the distal end section and causes the lever to tilt. The distal end section tilts together with the lever. An axial movement of the tilting tube in the proximal direction pulls the lever back and straightens the distal end section. The tilting mechanism is known from EP 2 377 477 B1.

According to another advantageous aspect of the present disclosure, a rotation of the second actuating member around its rotational axis rotates the distal end section around a rotational axis. The effector in the distal end section is also rotated around the rotational axis. Therefore, the jaw parts of the effector can be rotated and the effector can grab tissue in various positions. The rotational axis of the distal end section can be identical to the longitudinal axis of the shaft, if the distal end section is not tilted. If the distal end section is tilted, the rotational axis of the distal end section is identical to a longitudinal axis of the distal end section. The tilting angle may be provided between the longitudinal axis of the distal end section and the longitudinal axis of the shaft.

Preferably, the second actuating member is connected to the connector in a rotationally fixed manner and the connector is connected to a rotating tube in a rotationally fixed and axially displaceable manner. A rotation of the rotating tube can cause the distal end section to rotate around the longitudinal axis. The rotating tube may extend along the longitudinal axis of the shaft and run inside the tilting tube. The rotating tube may protrude from the tilting tube on the distal end and can be connected to the distal end section.

Preferably, the connector comprises protruding noses extending radially from the connector, preferably a base plate of the connector. The protruding noses lock into receiving openings in the collar of the second actuating member. The receiving openings are designed to connect the connector and the collar in a rotationally fixed and axially displaceable manner. Therefore, the rotation of the second actuating member is transmitted to the connector. Rotation of the connector may drive the rotating tube. It is noted that the collar can also comprise protruding noses fitting in receiving openings of the connector, preferably the base plate of the connector.

Preferably, the distal end section is rotatable around the longitudinal axis by the rotation of the second actuating member, when the distal end section is tilted by the rotation of the first actuating member. The rotation of the rotating tube can be transmitted to the distal end section, even if the distal end section is tilted from the longitudinal axis of the shaft.

Preferably, the activation tube extends inside the rotating tube. The rotating tube may extend inside the tilting tube. The tilting tube may extend inside the shaft. The inner tubes protrude from the respective outer tubes.

According to another advantageous aspect of the present disclosure, the second actuating member can be rested in a proximal position. The second actuating member is movable along the longitudinal axis from the distal position to the proximal position to actuate the effector. Preferably, the effector closes when the second actuating member is pulled from the distal to the proximal position. The second actuating member can be rested in the proximal position. That leaves the effector locked. The resting position ensures that the effector cannot open or close unwantedly. For example, a piece of tissue can be grabbed with the effector. Then, effector is locked in the closed position to hold onto the tissue and remove the tissue from the patient's body cavity.

The handle may comprise resting means resting the second actuating member in a resting position and preventing the second actuating member from the axial movement along the longitudinal axis. Preferably, the locking spring comprises a number of locking arms resting on a ramp of a socket so that an axial movement of the locking spring from a proximal position to a distal position is blocked. The socket may be mounted in the housing in a rotatable and axially fixed manner and surrounds the rotating tube. The blocked/rested locking spring ensures that the effector is closed while the second actuating member is still rotatable and moveable independently from the locking spring. The user can lock the effector in the resting position and is able to sequentially rotate the first and second actuating members without having to hold the second actuating member.

Preferably, the second actuating member is connected to the locking spring in an axially fixed manner while moving from the distal to the proximal position. The second actuating member comprises the shoulder, which moves the locking spring together with the second actuating member from the distal to the proximal position. However, the second actuating member and the locking spring are axially displaceable in the proximal position and during a movement from the proximal to the distal position. Thus, the second actuating member can rotate around its rotation axis in the resting position.

Preferably, the locking arms comprise pins that protrude on the side of the locking arms in opposite directions. Preferably, the second actuating member comprises a motion link, which lifts a pin of the locking arms over the ramp and unlocks the resting position. The operator/user pushes the second actuating member in the distal direction. The pins run in the motion link and the locking arms are lifted. The motion link does not lift the locking arms without the push against the second actuating member from the operator because the second actuating member and the locking spring are moveable independently from each other in the proximal position.

Preferably, the motion link has the shape of a hill. The hill is high enough to lift the locking arms over the resting ramp of the socket.

Preferably, the handle is rotational symmetric regarding its longitudinal axis. Therefore, the handle can be held and operated like a screwdriver. That means the user can turn the whole handle and the surgical instrument with it along its longitudinal axis by twisting the hand that holds the handle. This provides an easy and intuitive way to turn the surgical instrument around its longitudinal axis. By rotating the surgical instrument, the shaft of the instrument is rotated around its longitudinal axis. No further actuating member is required that rotates the shaft of the instrument relative to the handle. As the handle is rotational symmetric the user can hold the handle as he wants and as required by the operation. There is no constrained posture caused by the shape of the handle.

DETAILED DESCRIPTION OF THE FIGURES

Figure 1:
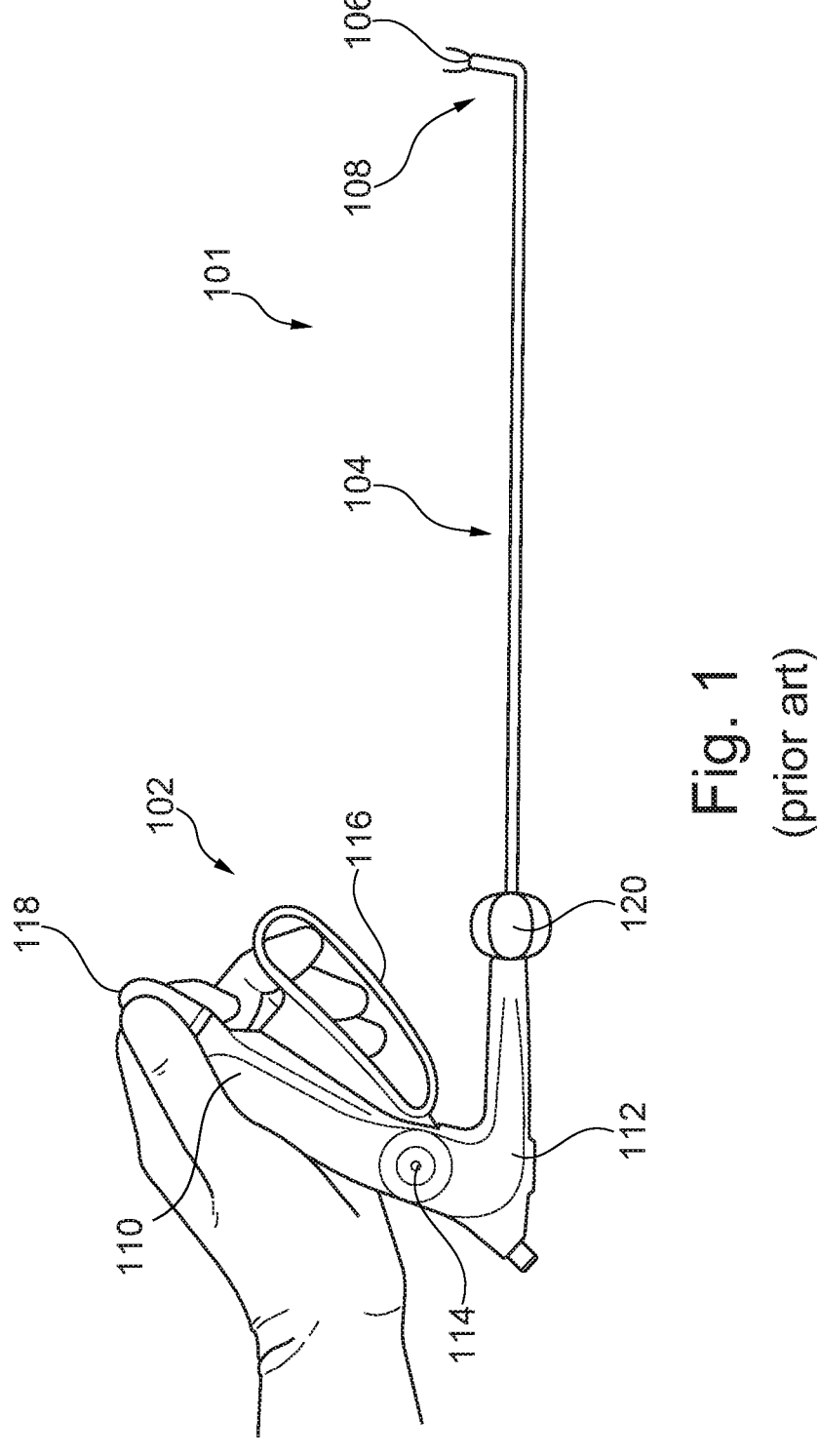
FIG. 1 shows a surgical instrument according to the prior art.

FIG. 1 shows a surgical instrument 101 according to the prior art. The configuration and the function of the surgical instrument 101 is in detail described in EP 2 377 477 B1. The instrument 101 comprises a proximal handle 102, a shaft 104 extending from the handle 102, and an effector 106 at the distal end section 108 of the shaft 104. The handle 102 has a C-shaped form or a C-shaped curve. A handle piece 110 is pivotably connected to the shaft 104 via a coupling member 112. The handle piece 110 is connected to the coupling member 112 by a hinge mechanism 114. Inclining the handle piece 110 in regards to the coupling member 112 or longitudinal axis of the shaft 104 deflects the distal end section 108 from the shaft direction. The handle piece 110 comprises a hand lever 116. Actuation of the hand lever 116 actuates the distal effector 106. The handle piece 110 further comprises a first rotary knob 118 at its proximal end.

Rotation of the first rotary knob 118 rotates the distal end section 108 around its longitudinal axis. The coupling member 112 comprises a second rotary knob 120. Rotation of the second rotary knob 120 rotates the shaft 102 around its longitudinal axis.

Figure 2:
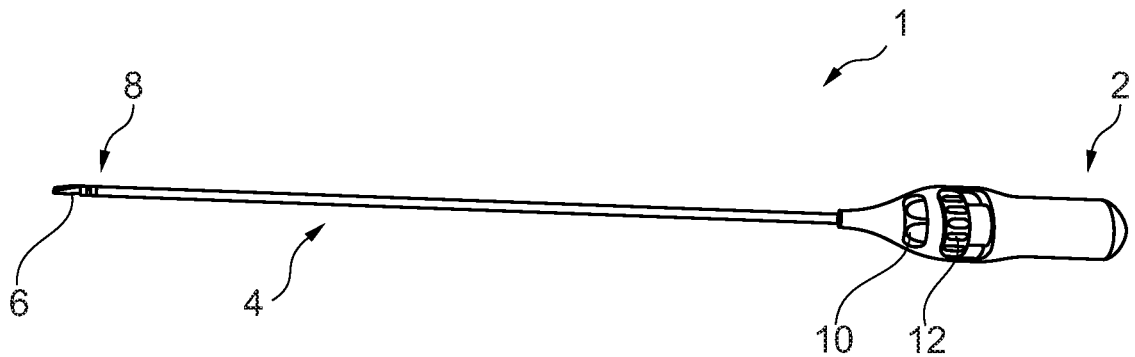
FIG. 2 shows a surgical instrument according to the present disclosure.

FIG. 2 shows a surgical instrument 1 according to the present disclosure. The surgical instrument 1 comprises a proximal handle 2, a shaft 4 extending from the handle 2 in a distal direction, and an (end-) effector 6 at the distal end section 8 of the shaft 4. The effector 6 is preferably a medical forceps or a scissor. The handle 2 comprises a first actuating member/first rotary knob 10 and a second actuating member/second rotary knob 12. The first actuating member 10 is positioned closer to a distal end of the handle 2. The first actuating member 10 is (exclusively) rotatable around a rotational axis, which is the longitudinal axis 14 of the shaft 4. The second actuating member 12 is rotatable around a rotational axis, which is preferably identical to the rotational axis of the first actuating member 10. The second actuating member 12 is also movable axially along the longitudinal axis 14 of the shaft 4 from a distal position to a proximal position and backwards.

A rotation of the first actuating member 10 around its rotational axis causes the distal end section 8 to tilt/bend in a bending or tilting plane (relative to the shaft 4). A rotation of the second actuating member 12 around its rotational axis causes the distal end section 8 and the effector 6 to rotate around the longitudinal axis 14 of the shaft 4 (relative to the shaft 4). An axial movement of the second actuating member 12 actuates the distal effector 6 (opening/closing movements). Preferably, the axial movement of the second actuating member 12 causes an open-closing movement of jaw parts of the medical forceps or scissor. When the second actuating member 12 is positioned in the distal position, the effector jaws are open. In the proximal position of the second actuating member 12, the effector jaws are closed.

Figure 3:
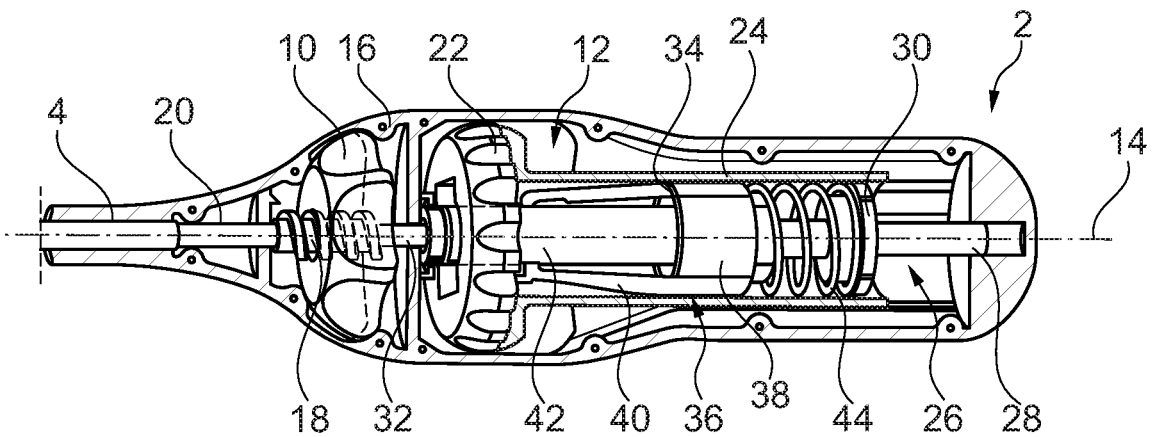
FIG. 3 shows a part-sectional view of a handle of the surgical instrument according to the present disclosure.
Figure 4:
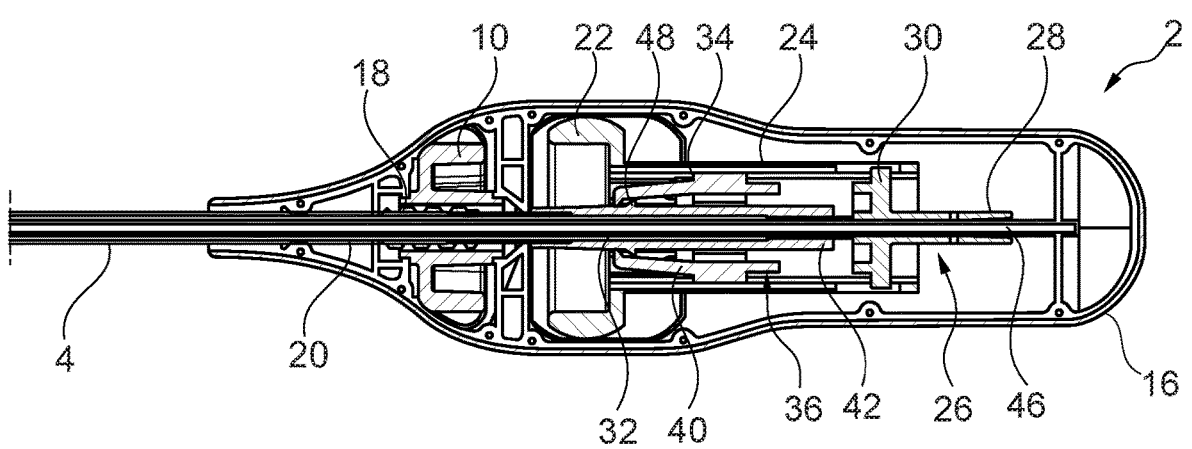
FIG. 4 shows a sectional view of the handle of the surgical instrument according to the present disclosure.

FIG. 3 shows a part-section through the handle 2 and FIG. 4 shows a section through the handle. The handle 2 comprises the first actuating member 10 and the second actuating member 12 which are both rotatable mounted in a housing 16 of the handle 2. The first actuating member 10, the second actuating member 12 and the housing 16 are all formed rotationally symmetric. The first actuating member 10 is a round wheel with a gripping section and is rotationally mounted in the housing 16. The first actuating member 10 is connected to a spindle/leadscrew 18 in a rotationally fixed manner. The leadscrew 18 transmits a rotational movement of the first actuating member 10 into a translational/axial movement. The leadscrew 18 is connected to a tilting tube (tilting bar) 20 in an axially fixed manner. The tilting tube 20 is a hollow tube/pipe/bar extending inside the shaft 4 from the leadscrew 18 towards the distal end section 8 of the shaft 4. The tilting tube 20 is permanently connected to the leadscrew 18, for example by gluing. When the first actuating member 10 is rotated around its rotational axis, the leadscrew 18 transmits the rotation into the translational movement along the longitudinal axis of the shaft 4 and therefore causes an axial/translational movement of the tilting tube 20. The tilting tube 20 is connected to a lever at its distal end. The lever causes the distal end section 8 of the shaft 4 to tilt/bend in the tilting plane. The tilting mechanism is know from EP 2 377 477 B1 and will not be described in detail in the present disclosure. The first actuating member 10 and the leadscrew 18 are self-locking to prevent an unwanted rotation of the first actuating member 10. Especially when the user releases the first actuating member 10 when the distal end section 8 is tilted the self-locking prevents the distal end section 8 from returning to its initial state.

The second actuating member 12 is rotatable around its rotational axis, too. The second actuating member 12 comprises a round actuation wheel 22 with a gripping section and a (tubular) collar 24 extending from the actuation wheel 22 in the proximal direction of the handle 2. The collar 24 is connected to a connector 26 in a rotationally fixed but axially free manner. The connector 26 is a rotational symmetric component with an elongated base member 28 and a thin base plate 30 protruding from the base member 28 in the radial outer direction. The base plate 30 comprises a number of latching noses/protrusions 56 protruding/projecting from its peripheral surface in the radial outer direction. The latching noses/protrusions 56 fit into a number of receiving openings/notches 58 in the collar 24 capable of receiving the latching noses 56. Therefore, the collar 24 drives the connector 26, but the connector 26 can move axially in regards to the collar 24.

The elongated base member 28 of the connector 26 surrounds a rotating tube 32 and is connected to the rotating tube 32 in a rotationally fixed and axially displaceable manner. The rotating tube 32 extends along the shaft 4 to the distal end section 8. The rotation of the rotating tube 32 causes the rotation of the distal end section 8 around the longitudinal axis 14. The effector 6 rotates together with the distal end section 8. The connection of the rotating tube 32 to the distal end section 8 and the effector 6 is already known from EP 2 377 477 B1. The rotating tube 32 extends inside the tilting tube 20 and protrudes out of the tilting tube 20 at the distal end.

The collar 24 of the second actuating member 12 comprises a shoulder 34 that is in contact with a locking spring 36. When the second actuating member 12 and its collar 24 are moved axially along the longitudinal axis of the handle, the locking spring 36 is moved together with the collar 24 in the proximal direction. A longitudinal axis of the locking spring 36 is identical to the longitudinal axis 14 of the handle 2. The locking spring 36 has a main body 38 that is rotationally symmetric and two locking arms 40 that extend from the main body 38 in the distal direction. The locking arms 40 are arranged on diametrically opposite sides of the rotational axis of the locking spring 36. The locking spring 36 is moveable along the longitudinal axis regarding a sleeve/socket 42 that extends along the longitudinal axis and surrounds the rotating tube 32. The socket 42 is mounted on the housing 16 in a rotatable and axially fixed manner. Preferably, the housing 16 comprises latches protruding from the housing 16 holding the socket 42 at its distal end.

The locking spring 36 is connected to a (wire) spring 44. The spring 44 is arranged in a way that its longitudinal axis is identical to the longitudinal axis 14 of the handle 2. When the locking spring 36 is moved by the collar 24 in the proximal direction of the handle 2 along its longitudinal axis, the spring 44 is compressed. On its proximal side, the spring 44 is connected to the connector 26. When the spring 44 is fully compressed, the connector 26 is also moved in the proximal direction by the locking spring 36. As the connector 26 is connected to an actuation tube/actuation bar 46 in a fixed manner, the actuation tube 46 is moved axially with the movement of the connector 26. The actuation tube 46 extends from the handle 2 to the distal effector 6 and actuates the effector 6. Therefore, the axial movement of the second actuating member 12 actuates the distal effector 6.

Along the longitudinal axis of the handle 2 extend a number of tubes. The actuation tube 46 is the tube on the inner side of the tubes. The actuation tube 46 is mounted in the housing 16 at its proximal end. The rotating tube 32 surrounds the actuation tube 46. The tilting tube 20 surrounds the rotating tube 32. The outer most level of the tubes is the shaft 4.

The sleeve/socket 42 surrounds the actuation tube 46 and the rotating tube 32 and comprises two ramps 48 that protrude in a radial outer direction from the outer surface of the socket 42. The two ramps 48 are arranged on diametrically opposite sides of the longitudinal axis. When the locking spring 36 is moved axially regarding the socket 42 in a proximal direction, the locking arms 40 of the locking spring 36 jump above the ramps 48. In other words, the locking spring is moved in a way that the effector 6 closes. The locking arms 40 jump over the respective ramp 48 during the movement in the proximal direction. The ramps 48 are not symmetrically shaped. The proximal slope of each ramp 48 is much steeper than the distal slope. Therefore, the locking arms 40 can jump over the ramps 48 in the proximal direction but cannot jump over the ramps 48 in the opposite distal direction. Therefore, the locking spring 36 is locked in its proximal position. The locking spring 36 unable to reverse back in the distal position comprises the resting mechanism of the handle 2. The second actuating member 12 is locked in its proximal position. Therefore, the effector 6 is locked/rested in its closed position. The second actuating member 12 is rotatable independently of the resting mechanism.

Figure 5:
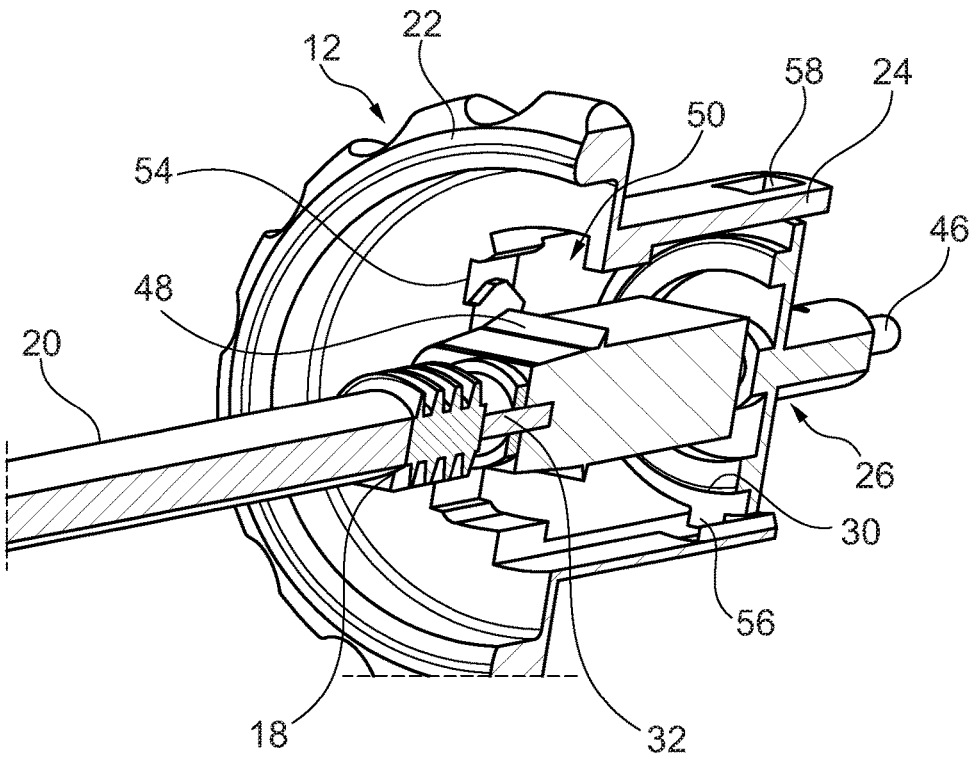
FIG. 5 shows a isometric view of a second actuating member.

When the resting mechanism of the second actuating mechanism 12 should be unlocked, the operator moves the second actuating member 12 in the distal direction. The second actuating member 12 comprises a cavity 50 in which the locking arms 40 are placed. The locking arms 40 comprise pins 52 protruding sideways from the locking arms in opposite direction. The cavity 50 of the second actuating member 12 comprises a motion link 54 in which the pins 52 of the locking arms 40 run. The motion link 54 is shown in FIG. 5 and has a hill-shaped form. When the pins 52 run in the motion link 54, the pins 52 are lifted together with the locking arms 40 and the are lifted over the ramps 48 on the socket 42. Thus, the locking arms 40 can cross the resting ramps 48 and the resting mechanism is unlocked. FIG. 5 shows a longitudinal section through the second actuating member 12 with the motion link 54, the socket 42 with the ramp 48 and the connector 26.

The locking arms 40 and the ramp 48 are positioned in the cavity 50 of the second actuating member 12 in such a way that the locking spring 36 and the socket 42 rotate with the second actuating member 12. However, the socket is not connected to the rotating tube 32 that extends inside the socket 42.

The plate member 30 of the connector 26 comprises protruding noses 56 engaging in a receiving opening 58 of the collar 24 of the second actuating member 12. The protruding noses 56 and the receiving openings 58 are formed that the collar 24 and the connector 26 are rotatable connected but axially independently.

Figure 6:
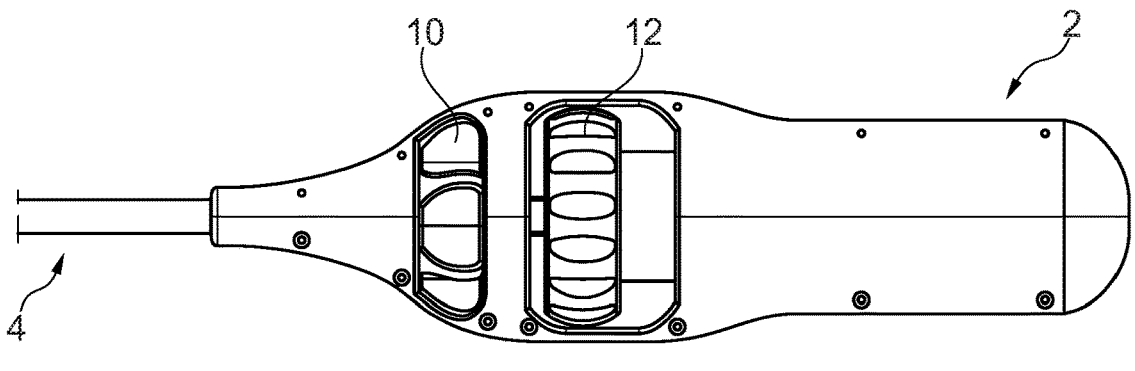
FIG. 6 shows a side view of the handle of the surgical instrument according to the present disclosure.
Figure 7:
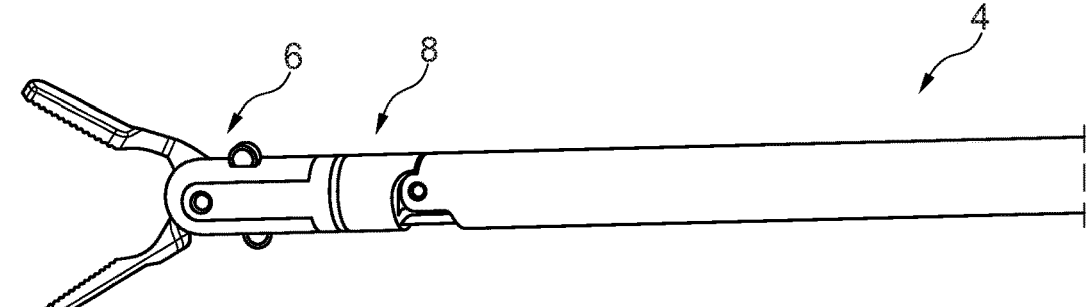
FIG. 7 shows a detailed view of an open effector.

FIG. 6 shows the handle 2 with the second actuating member 12 in a distal position. In the distal position, the effector 6 at the distal end section 8 of the shaft 4 is open, as it is shown in FIG. 7. The second actuating member 12 is rotatable freely in the distal position.

Figure 8:
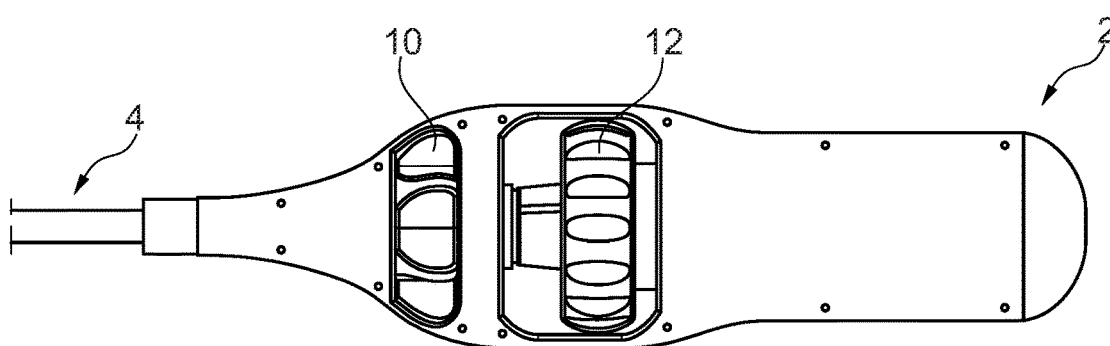
FIG. 8 shows a side view of the handle of the surgical instrument according to the present disclosure with the second actuating member in a proximal position.
Figure 9:
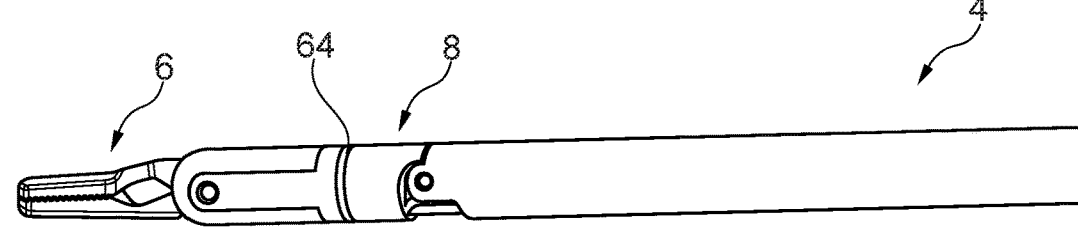
FIG. 9 shows a detailed view of a closed effector.

FIG. 8 shows the handle 2 with the second actuating member 12 in the proximal position. In the proximal position, the effector 6 at the distal end section 8 of the shaft 4 is closed, as it is shown in FIG. 9. The second actuating member 12 is rotatable freely in the proximal position. The effector 6 is closed by the movement of the second actuating member 12 in the proximal direction. The distal end section 8 with the effector 6 is rotatable around its longitudinal axis. The rotatable distal end section 8 is connected to the shaft 4 by a rotatable coupler 64.

Figure 10:
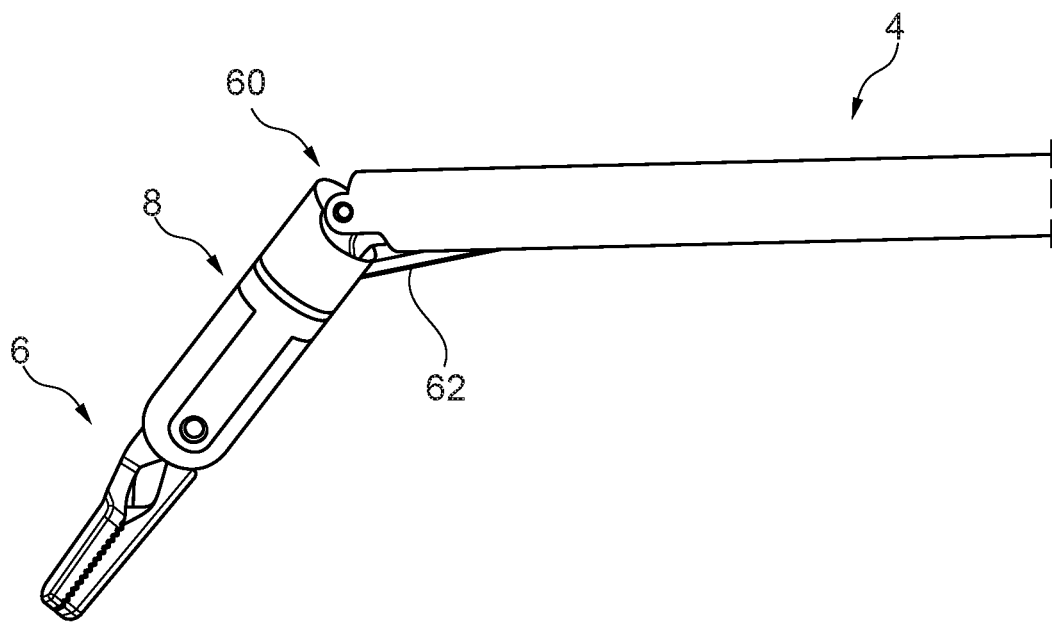
FIG. 10 shows a detailed view of a tilted distal end section with an open effector.
Figure 11:
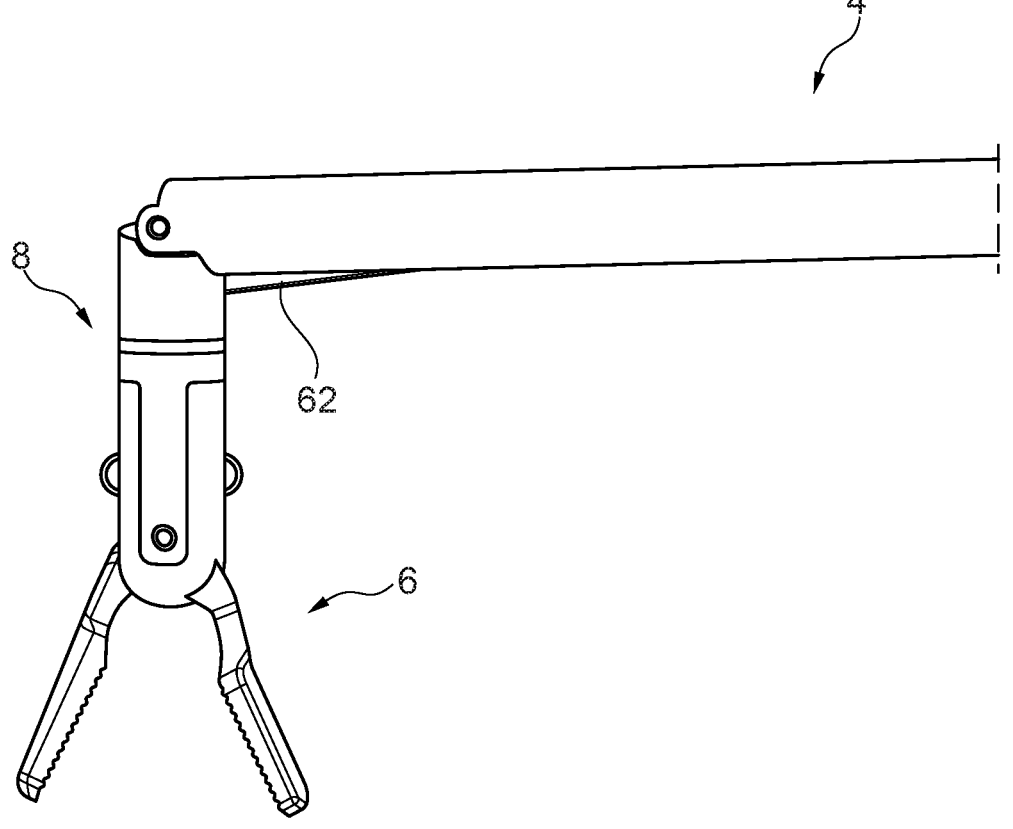
FIG. 11 shows a detailed view of a tilted distal end section with a closed effector.

FIG. 10 shows a tilted distal end section 8 of the shaft 4 with a closed effector 6. FIG. 11 shows a tilted distal end section 8 of the shaft 4 with an open effector 6. It is noted that the distal end section 8 is rotatable around its rotatable axis even when the distal end section 8 is tilted. The distal end section 8 is connected to the rest of the shaft 4 by a joint 60. The tilting mechanism for the distal end section 8 comprises a hinge lever 62 connecting the shaft 4 and the distal end section 8. The tilting mechanism is known for example from EP 2 377 477 B1 such reference can be made thereto at this point.

LIST OF REFERENCE SIGNS 1 surgical instrument
2 handle
4 shaft
6 effector
8 distal end section
10 first actuating member
12 second actuating member
14 longitudinal axis
16 housing
18 leadscrew
20 tilting tube
22 actuating wheel
24 collar
26 connector
28 base member
30 base plate
32 rotating tube
34 shoulder
36 locking spring
38 main body
40 locking arms
42 socket
46 actuation tube
48 ramp
50 cavity
52 pin
54 motion link
56 protruding nose
58 receiving opening
60 joint
62 hinge lever
101 surgical instrument
102 handle
104 shaft
106 effector
108 distal end section
110 hand piece
112 coupling member
114 hinge mechanism
116 hand lever
118 rotary knob
120 second rotary knob

The invention claimed is:

1. A surgical instrument comprising:
a handle;
a shaft extending from the handle into a distal direction along a longitudinal axis; and
a medical forceps or scissor at a distal end of the shaft, wherein the handle comprises a plurality of manual actuating members configured to manipulate the medical forceps or scissor for rotating, tilting and open-closing movements, and the plurality of manual actuating members comprises:

a first actuating member being rotatable around a first rotational axis that is collinear or parallel with the longitudinal axis of the shaft, a second actuating member being rotatable around a second rotational axis that collinear or parallel with the longitudinal axis of the shaft, the second actuating member being movable along the longitudinal axis of the shaft, wherein a rotation of the second actuating member relative to the handle rotates a distal end section of the shaft with the medical forceps or scissor around the longitudinal axis, and wherein an axial movement of the second actuating member causes the open-closing movements of jaw parts of the medical forceps or scissor.

2. The surgical instrument according to claim 1, wherein the second actuating member is connected to a locking spring in an axially fixed manner and transmits the axial movement to the locking spring.

3. The surgical instrument according to claim 2, wherein the locking spring is connected to a spring in an axially fixed manner and the axial movement of the locking spring compresses the spring.

4. The surgical instrument according to claim 1, wherein the axial movement of the second actuating member is transmitted to an actuation tube via a locking spring, a compressed spring and a connector and an axial movement of the actuation tube actuates the medical forceps or scissor.

5. The surgical instrument according to claim 4, wherein the axial movement of the actuation tube closes jaw parts of the medical forceps or scissor with a movement in the proximal direction and opens the jaw parts with a movement in the distal direction.

6. The surgical instrument according to claim 1, wherein a rotation of the first actuating member tilts a distal end section of the shaft in a tilting plane.

7. The surgical instrument according to claim 6, wherein the first actuating member is connected to a leadscrew transmitting the rotation of the first actuating member into a translational movement.

8. The surgical instrument according to claim 7, wherein the leadscrew is connected to a tilting tube extending in the shaft that moves axially along the longitudinal axis of the shaft.

9. The surgical instrument according to claim 6, wherein the distal end section is rotatable around its longitudinal axis by the rotation of the second actuating member, when the distal end section is tilted by the rotation of the first actuating member.

10. The surgical instrument according to claim 1, wherein the second actuating member is connected to a connector in a rotationally fixed manner and the connector is connected to a rotating tube in a rotationally fixed and axially displaceable manner and a rotation of the rotating tube causes the distal end section to rotate around the longitudinal axis.

11. The surgical instrument according to claim 1, wherein the handle comprises resting means resting the second actuating member in a resting position and preventing the second actuating member from the axial movement along the longitudinal axis.

12. The surgical instrument according to claim 11, wherein the resting means comprises a locking spring comprising at least one locking arm resting on a ramp of a socket so that an axial movement of the locking spring from a proximal position to a distal position is blocked.

13. The surgical instrument according to claim 11, wherein the second actuating member comprises at least one motion link, which lifts pins of at least one locking arm over a ramp of a socket and unlocks the resting position while moving from the proximal to the distal direction.

14. The surgical instrument according to claim 1, wherein the handle is rotational symmetric regarding the longitudinal axis.

15. The surgical instrument according to claim 1, wherein the plurality of manual actuating members consists of:

the first actuating member, and the second actuating member.

* * * * *